US00PP27443P3

(12) United States Plant Patent
Bak et al.

(10) Patent No.: US PP27,443 P3
(45) Date of Patent: Dec. 6, 2016

(54) ***MEDINILLA* HYBRID PLANT NAMED 'ROYAL PEARLZ'**

(50) Latin Name: ***Medinilla* hybrid**
Varietal Denomination: ROYAL PEARLZ

(71) Applicants: Elly Bak, Assendelft (NL); Nicolas Steur, Assendelft (NL)

(72) Inventors: Elly Bak, Assendelft (NL); Nicolas Steur, Assendelft (NL)

(73) Assignee: Corn Bak B.V. (NL)

( * ) Notice: Subject to any disclaimer, the term of this patent is extended or adjusted under 35 U.S.C. 154(b) by 202 days.

(21) Appl. No.: 13/999,857

(22) Filed: Mar. 28, 2014

(65) Prior Publication Data

US 2015/0282403 P1 Oct. 1, 2015

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

PUBLICATIONS

PLUTO Plant Variety Database Jul. 22, 2015 p. 1.*

* cited by examiner

*Primary Examiner* — Annette Para
(74) *Attorney, Agent, or Firm* — Cassandra Bright

(57) ABSTRACT

A new and distinct *Medinilla* sp. plant named 'ROYAL PEARLZ', characterized by an erect shrub plant, measuring about 30 cm in total height (when first flowering) and about 45-70 cm in diameter; green colored leaves measuring about 15-20 cm in length and about 10-20 cm in width; pendulous panicle, measuring about 36 cm in length and about 15 cm in diameter, with red-purple (RHS 72C) flowers.

2 Drawing Sheets

Latin name of the genus and species: *Medinilla* hybrid.
Variety denomination: 'ROYAL PEARLZ'.

BACKGROUND OF THE INVENTION

The present invention relates to a new and distinct hybrid cultivar of *Medinilla* plant, botanically known as *medinilla* sp., hereinafter referred to by the cultivar name 'ROYAL PEARLZ'. The genus of *Medinilla* belongs to the Melastimataceae family.

The new *Medinilla* 'ROYAL PEARLZ' is a product of a planned breeding program conducted by the inventor, Ely Bak and Nico D. M. Steur, in Assendelft, The Netherlands. The objective of the breeding program is to develop a new *Medinilla* variety with good growing habit and attractive inflorescence.

The New *Medinilla* 'ROYAL PEARLZ' originated from a cross made in the controlled breeding progeam by the inventors in 2008, in Assendelft, The Netherlands. The female or seed parent is the *Medinilla* selection designated '834918227' (unpatented). 'ROYAL PEARLZ' was discovered and selected by the inventors in 2010, as a single flowering plant within the progeny of the stated cross in a controlled environment in Assendelft, The Netherlands.

Asexual reproduction of the new *Medinilla* hybrid 'ROYAL PEARLZ' performed by vegetative means by cuttings was first performed in 2010, in Assendelft, The Netherlands. The first 'ROYAL PEARLZ' plants propagated through the use of the cuttings flowered in 2011, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'ROYAL PEARLZ' which in combination distinguish this *Medinilla* hybrid as a new and distinct cultivar:

1. Solid growth habit.
2. Erect shrub plant, measuring about 30 cm in height (above the pot when first flowering);
3. Green colored leaves, measuring about 15-20 cm in length and about 10-20 cm in width;
4. Pendulous panicles with red-purple (RHS 72C) colored flowers;

COMMERCIAL COMPARISON

Of the many commercial cultivars known to the present inventors, the most similar in comparison to the new *Medinilla* 'ROYAL PEARLZ' is the *Medinilla* 'MAGNIFICA'. Plants of the new *Medinilla* 'ROYAL PEARLZ' differ from plants of *Medinilla* 'MAGNIFICA' primarily in leaf size and bract size. Plants of 'ROYAL PEARLZ' have smaller leaves and smaller sized bracts than plants of "MAGNIFICA'.

PARENT COMPARISON

Plants of the new *Medinilla* 'ROYAL PEARLZ' differ from plants of the female parent in inflorescence. The new variety produces more inflorescences per plant. Additionally, inflorescences of the new variety are darker than those of the seed parent.

Plants of the new *Medinilla* 'ROYAL PEARLZ' differ from plants of the male parent in plant habit. Plants of the new variety are significantly more compact than plants of the pollen parent.

BRIEF DESCRIPTION OF THE PHOTOGRAPHS

The accompanying photograph illustrates the overall appearance of the new *Medinilla* 'ROYAL PEARLZ' showing the colors as true as is reasonably possible with colored reproductions of this type. Colors in the photograph may differ slightly from the color values cited in the detailed botanical description which accurately describes the color of 'ROYAL PEARLZ'.

DETAILED BOTANICAL DESCRIPTION

Figure 1:
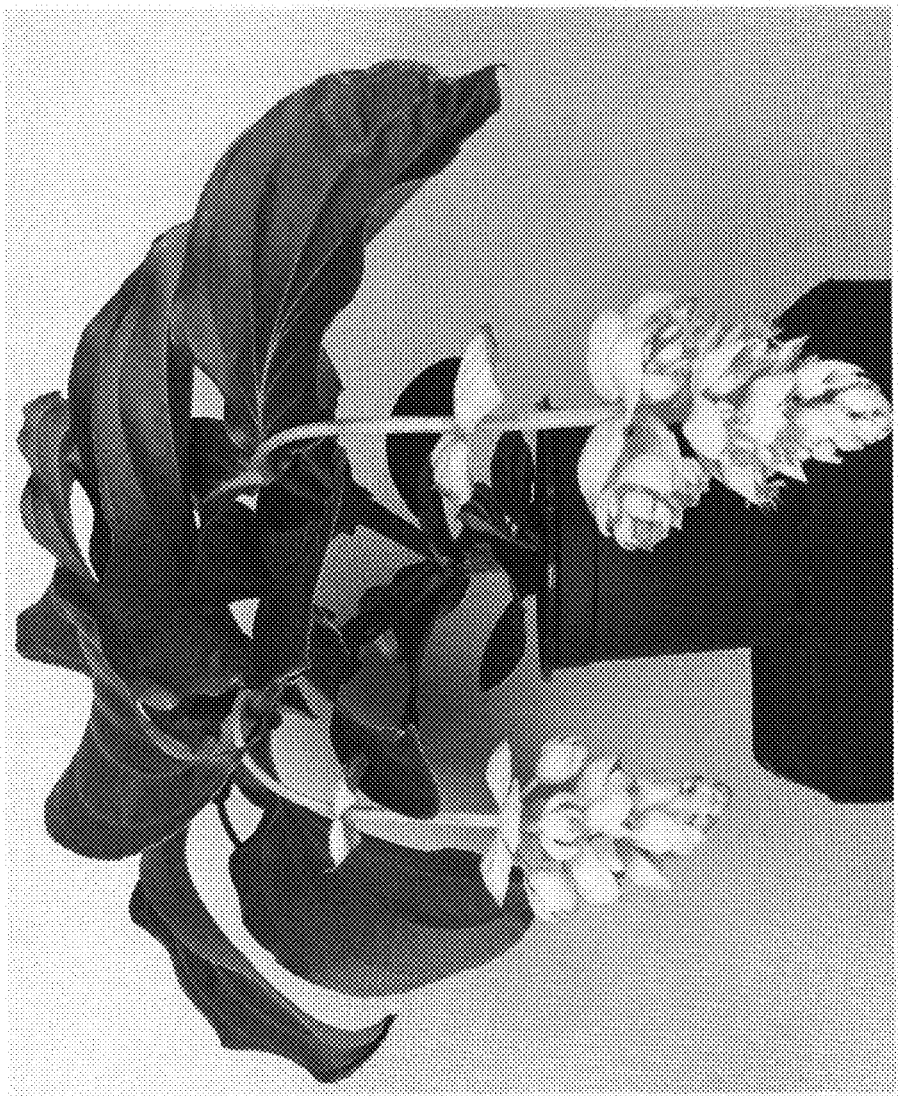
FIG. 1 shows a side view perspective of a typical potted flowering plant of 'ROYAL PEARLZ' at about 50 weeks from potting.
Figure 2:
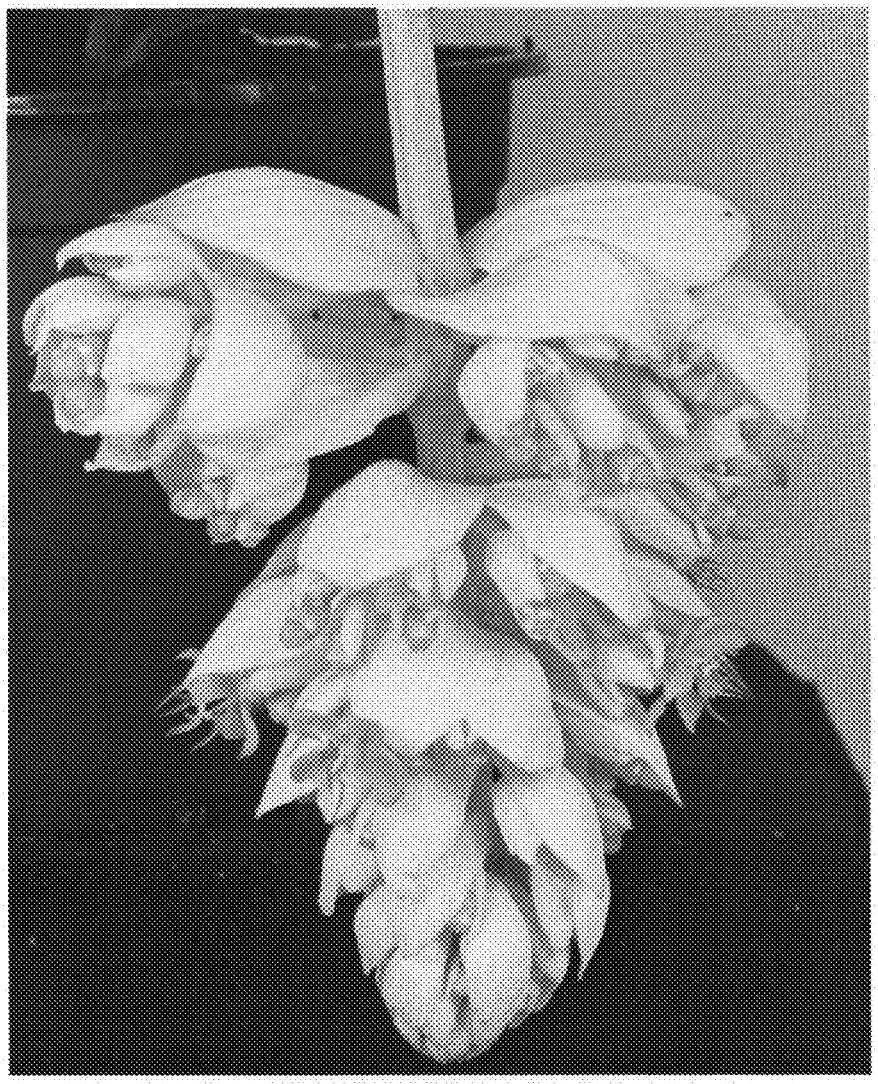
FIG. 2 shows a close-up view of a typical inflorescence of 'ROYAL PEARLZ'.

'ROYAL PEARLZ' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Medinilla* "ROYAL PEARLZ' as grown in a greenhouse in Assendelft, The Netherlands, under conditions which closely approximate those generally used in commercial practice.

Color references are made to The Royal Horticultural Society Colour Chart (R.H.S.), 2001 Edition, except where general colors of ordinary significance are used. Color values were taken under daylight conditions in a greenhouse in Assendelft, The Netherlands. The age of the plants of 'ROYAL PEARLZ' described is about 50 weeks from potting.

Classification:

*Botanical.*—*Medinilla* sp.

Parentage:

*Female parent.*—*Medinilla* selection designated '834918227' (unpatented).

*Male parent.*—*Medinilla* selection designated '834917015' (unpatented).

Propagation: Cuttings.

Plant:

*General appearance and form.*—Height: About 30 cm. Diameter: About 45-70 cm. Shape: Erect shrub.

*Growth habit.*—Stem.

*Plant vigor.*—Good.

*Flowering season.*—From April till October.

*Cold tolerance.*—Frost tender, temperatures below 5 C may damage plants.

*Fragrance.*—None.

Foliage:

*Quantity.*—About 18.

*Size.*—Length: About 15-20 cm. Width: About 10-20 cm.

*Overall shape.*—Elliptical.

*Apex shape.*—Cuspidate.

*Base shape.*—Acute.

*Margin.*—Slightly Undulate.

*Texture.*—Smooth.

*Color.*—Leaf color can vary somewhat depending on growing conditions. Upper Surface: Glossy green, ranges between RHS 137A and RHS 139A. Lower Surface: Green, closest to RHS 143C.

*Venation.*—Sunken.

Inflorescence:

*Shape.*—Pendulous panicles.

*Amount.*—About 4 (depending on the size of the plant).

*Size.*—Length: About 36 cm (including peduncle). Width: About 15 cm.

*Color.*—Red-purple, closest to RHS 72C.

*Corolla.*—Number: more than 150 per panicle.

*Petals.*—Number: 5 per flower. Length: 12 mm. Width: 7 mm. Overall Shape: obovate, asymmetrical. Apex Shape: obtuse. Color: Upper Surface: red-purple, closest to RHS 72C. Lower Surface: red-purple, closest to RHS 72C. Sepals: growth together, enclosing the ovary. Color: red-purple, closest to RHS 65A. Bracts: Quantity: 2-4 per crown. Arrangement: verticillate. Size: Length: about 1-5 cm. Width: 7 mm-5.5 cm. Overall Shape: elliptical.

Reproductive organs:

*Androecium.*—Stamen: Number: 10 per flower. Length: 10 mm. Diameter: 1 mm. Color: light yellow, with a white base (too small to qualify RHS value). Anther: Length: 8 mm. Color: violet, closest to RHS 88B, with a yellow base (too small to qualify RHS value). Pollen: not visible. Gynoecium: Pistil: Number: 1 per flower. Length: 19 mm. Stigma: Width: <1 mm. Color: white, too small to qualify RHS value. Style: Length: 16 mm. Color: White, closest to RHS 155B. Ovary: Shape: round. Position: inferior. Length: 4 mm. Diameter: 4 mm. Color: white closest to RHS 155C.

Seeds: No seeds produced.

Fruits: No fruit produced.

Disease/pest resistance: No observations made.

Disease/pest susceptibility: No observations made.

What is claimed is:

1. A new and distinct *Medinilla* plant named 'ROYAL PEARLZ', as illustrated and described herein.

* * * * *